US007960575B2

(12) United States Patent
Fenyvesi et al.

(10) Patent No.: US 7,960,575 B2
(45) Date of Patent: Jun. 14, 2011

(54) SYNTHESIS OF MONO AND DI ESTERS FROM BIOLOGICALLY-PRODUCED 1,3-PROPANEDIOL

(75) Inventors: Gyorgyi Fenyvesi, Wilmington, DE (US); Raja Hari Prasad R. Poladi, Bear, DE (US)

(73) Assignee: DuPont Tate & Lyle Bio Products Company, LLC, Wilmington, DE (US)

( * ) Notice: Subject to any disclaimer, the term of this patent is extended or adjusted under 35 U.S.C. 154(b) by 935 days.

(21) Appl. No.: 11/705,245

(22) Filed: Feb. 12, 2007

(65) Prior Publication Data

US 2007/0202580 A1      Aug. 30, 2007

Related U.S. Application Data

(60) Provisional application No. 60/772,471, filed on Feb. 10, 2006, provisional application No. 60/772,194, filed on Feb. 10, 2006, provisional application No. 60/772,193, filed on Feb. 10, 2006, provisional application No. 60/772,111, filed on Feb. 10, 2006, provisional application No. 60/772,120, filed on Feb. 10, 2006, provisional application No. 60/772,110, filed on Feb. 10, 2006, provisional application No. 60/772,112, filed on Feb. 10, 2006, provisional application No. 60/846,948, filed on Sep. 25, 2006, provisional application No. 60/853,920, filed on Oct. 24, 2006, provisional application No. 60/859,264, filed on Nov. 15, 2006, provisional application No. 60/872,705, filed on Dec. 4, 2006, provisional application No. 60/880,824, filed on Jan. 17, 2007.

(51) Int. Cl.
*C11C 1/00* (2006.01)
(52) U.S. Cl. .................... 554/168; 435/134
(58) Field of Classification Search .............. 554/168; 435/134
See application file for complete search history.

(56) References Cited

U.S. PATENT DOCUMENTS

| 5,633,362 A | 5/1997 | Nagarajan et al. |
| 5,686,276 A | 11/1997 | Laffend et al. |
| 5,716,676 A * | 2/1998 | Schutze et al. ............. 427/385.5 |
| 5,821,092 A | 10/1998 | Nagarajan et al. |

(Continued)

FOREIGN PATENT DOCUMENTS

JP      2002138069      5/2002

OTHER PUBLICATIONS

Chen, et al. "Cyclization During Polyesterifications: Isolation Of An 18-Member Ring Compound From Reaction of Phthalic Anhydride With 2,2-Dimethyl-1,3-Propanediol"; Journal of Applied Polymer Science, 1990, vol. 41, Issue 9-10, pp. 2517-2520.

(Continued)

*Primary Examiner* — Deborah D Carr
(74) *Attorney, Agent, or Firm* — McCarter & English

(57) ABSTRACT

A process for forming an ester from 1,3-propanediol comprising providing 1,3-propanediol with at least 90% biobased carbon, contacting the 1,3-propanediol with an acid, thereby forming the ester, and recovering the ester is provided. The acid can be an organic acid. Additionally, a process for producing an ester, either or both a monoester and a diester, from biologically-produced 1,3-propanediol is provided. This process includes providing 1,3-propanediol produced biologically through fermentation and catalytic conversion of atmospheric carbon, contacting the 1,3-propanediol with an organic acid, wherein said ester is produced; and recovering the ester. In this process the 1,3-propanediol can have has at least 95% biobased carbon, or can have 100% biobased carbon.

22 Claims, 7 Drawing Sheets

U.S. PATENT DOCUMENTS

| | | | |
|---|---|---|---|
| 6,025,184 | A | 2/2000 | Laffend et al. |
| 6,136,576 | A | 10/2000 | Diaz-Torres et al. |
| 6,255,442 | B1 | 7/2001 | Kurian et al. |
| 6,358,716 | B1 | 3/2002 | Bulthuis et al. |
| 6,361,983 | B1 | 3/2002 | Ames |
| 6,406,895 | B1 | 6/2002 | Defretin et al. |
| 6,428,767 | B1 | 8/2002 | Burch et al. |
| 6,479,716 | B2 | 11/2002 | Hilaly et al. |
| 6,555,700 | B1 | 4/2003 | Horrobin et al. |
| 6,576,340 | B1 * | 6/2003 | Sun et al. .................. 428/373 |
| 6,726,887 | B1 | 4/2004 | Sugarman |
| 7,098,368 | B2 | 8/2006 | Seapan et al. |
| 2004/0105899 | A1 | 6/2004 | Dowdle et al. |
| 2005/0020805 | A1 | 1/2005 | Sunkara et al. |
| 2005/0069997 | A1 | 3/2005 | Adkesson et al. |
| 2005/0154114 | A1 | 7/2005 | Hale |
| 2006/0035808 | A1 | 2/2006 | Ahmed et al. |
| 2006/0110810 | A1 | 5/2006 | Rajgarhia et al. |
| 2006/0148053 | A1 | 7/2006 | Emptage et al. |

OTHER PUBLICATIONS

"Industrial Bioproducts: Today and Tomorrow" (Paster et al.) Prepared by Energetics, Inc. for the US Department of Energy, Jul. 2003, See p. 1 and 2, Table 1-1 and 1-6.

Chaudhari, et al. "Diol-esters—A Family of Potential Plant Growth Regulators", Proc. Indian Acad. Sci. (Plant Sci.) vol. 96, No. 5, Nov. 1986, pp. 393-400.

Fung, et al. "Evolution of Carbon Sinks in a Changing Climate"; PNAS, Aug. 9, 2005, vol. 12, No. 32; pp. 11201-11206.

* cited by examiner

SYNTHESIS OF MONO AND DI ESTERS FROM BIOLOGICALLY-PRODUCED 1,3-PROPANEDIOL

CROSS REFERENCE TO RELATED APPLICATIONS

The present application claims the benefit of U.S. Provisional Application Ser. No. 60/772,471, filed Feb. 10, 2006; U.S. Provisional Application No. 60/772,194, filed Feb. 10, 2006, U.S. Provisional Application No. 60/772,193, filed Feb. 10, 2006, U.S. Provisional Application No. 60/772,111, filed Feb. 10, 2006, U.S. Provisional Application No. 60/772,120, filed Feb. 10, 2006, U.S. Provisional Application No. 60/772,110, filed Feb. 10, 2006, U.S. Provisional Application No. 60/772,112, filed Feb. 10, 2006, U.S. Provisional Application No. 60/846,948, filed Sep. 25, 2006, U.S. Provisional Application No. 60/853,920, filed Oct. 24, 2006, U.S. Provisional Application No. 60/859,264, filed Nov. 15, 2006, U.S. Provisional Application No. 60/872,705, filed Dec. 4, 2006 and U.S. Provisional Application No. 60/880,824, filed Jan. 17, 2007, the disclosures of which are expressly incorporated herein by reference in their entirety.

FIELD OF THE INVENTION

The field of the invention relates generally to the synthesis of organic esters, and more specifically to the synthesis of esters based on biologically-derived 1,3-propanediol.

BACKGROUND OF THE INVENTION

Consumers and manufacturers are increasingly concerned with the environmental impact of all products. The effort towards environmental impact awareness is a universal concern, recognized by government agencies. The Kyoto Protocol amendment to the United Nations Framework Convention on Climate Change (UNFCCC) currently signed by 156 nations is one example of a global effort to favor safer environmental manufacturing over cost and efficiency. Especially when applied to goods such as personal care, cosmetics, therapeutics and cosmecuticals, consumers are increasingly selective about the origins of the products they purchase. The 2004 Co-operative Bank's annual Ethical Consumerism Report (www.co-operativebank.co.uk) disclosed a 30.3% increase in consumer spending on ethical retail products (a general classification for environmental safe, organic and fair trade goods) between 2003 and 2004 while total consumer spending during the same period rose only 3.7%.

One of the single greatest environmental concerns to consumers is the global warming effect and greenhouse gases that contribute to the effect. Greenhouse gases are gases that allow sunlight to enter the atmosphere freely. When sunlight strikes the Earth's surface, some of it is reflected back towards space as infrared radiation. Greenhouse gases absorb this infrared radiation and trap the heat in the atmosphere. Over time, the amount of energy sent from the sun to the Earth's surface should be about the same as the amount of energy radiated back into space, leaving the temperature of the Earth's surface roughly constant. However, increasing the quantity of greenhouse gases above the quantity that existed before the rise of human industrialization is thought to increase the retained heat on the Earth's surface and produce the global warming observed in the last two centuries.

Carbon dioxide is singled out as the largest component of the collection of greenhouse gases in the atmosphere. The level of atmospheric carbon dioxide has increased 50% in the last two hundred years. Any further addition of carbon dioxide to the atmosphere is thought to further shift the effect of greenhouse gases from stabilization of global temperatures to that of heating. Consumers and environmental protection groups alike have identified industrial release of carbon into the atmosphere as the source of carbon causing the greenhouse effect. Only organic products composed of carbon molecules from renewably based sources such as plant sugars and starches and ultimately atmospheric carbon are considered to not further contribute to the greenhouse effect, when compared to the same organic molecules that are petroleum or fossil fuel based.

In addition to adding carbon dioxide to the atmosphere, current methods of industrial production of propanediols produce contaminants and waste products that include among them sulfuric acid, hydrochloric acid, hydrofluoric acid, phosphoric acid, tartaric acid, acetic acids, alkali metals, alkaline earth metals, transitional metals and heavy metals, including iron, cobalt, nickel, copper, silver, molybdenum, tungsten, vanadium, chromium, rhodium, palladium, osmium, iridium, rubidium, and platinum (U.S. Pat. Nos. 2,434,110, 5,034,134, 5,334,778, and 5,10,036).

There is a need for all manufactures to provide products reduced environmental impacts, and to especially consider the carbon load on the atmosphere. There is also an environmental advantage for manufacturers to provide products of renewably based sources. Further, there is a need for a proven solvent which is produced with no or little increase to the present carbon-dioxide level in the environment.

Published U.S. Patent Application No. 2005/0069997 discloses a process for purifying 1,3-propanediol from the fermentation broth of a cultured *E. coli* that has been bioengineered to synthesize 1,3-propanediol from sugar. The basic process entails filtration, ion exchange and distillation of the fermentation broth product stream, preferably including chemical reduction of the product during the distillation procedure. Also provided are highly purified compositions of 1,3-propanediol.

SUMMARY OF THE INVENTION

A process for forming an ester from 1,3-propanediol comprising providing 1,3-propanediol with at least 90% biobased carbon, contacting the 1,3-propanediol with an acid, thereby forming the ester, and recovering the ester is provided. The acid can be an organic acid. Additionally, a process for producing an ester, either or both a monoester and a diester, from biologically-produced 1,3-propanediol is provided. This process includes providing 1,3-propanediol produced biologically through fermentation and catalytic conversion of atmospheric carbon, contacting the 1,3-propanediol with an organic acid, wherein said ester is produced; and recovering the ester. In this process the 1,3-propanediol can have has at least 95% biobased carbon, or can have 100% biobased carbon.

BIOLOGICAL DEPOSITS

Figure 1:
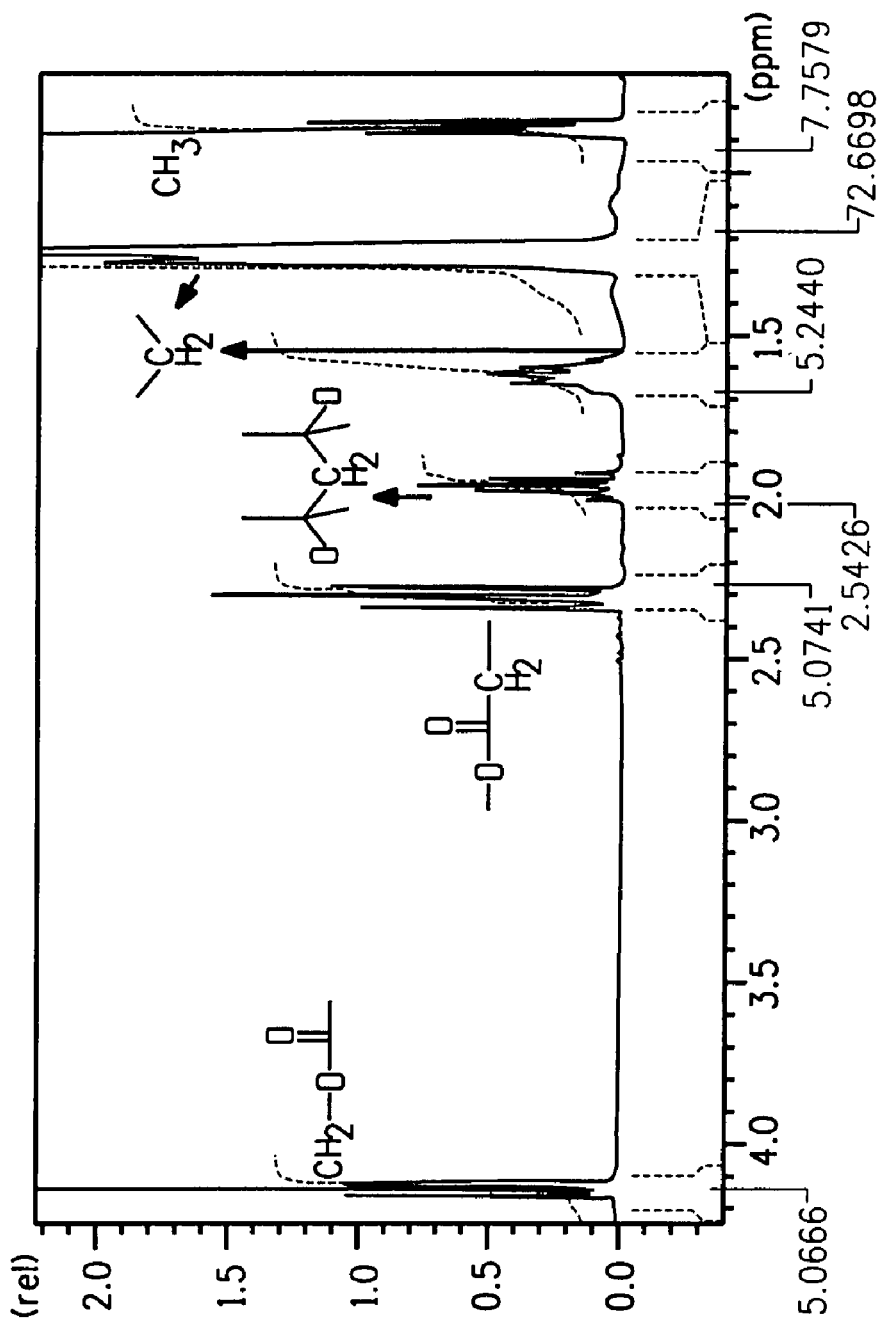
FIG. 1 is diagram of nuclear magnetic resonance spectra of the products obtained in Example 3. The figure plots the following values: ($CDCl_3$): $\delta$=0.88 (t, $CH_3$—$CH_2$, 6H), 1.26 (t, $CH_2$—$CH_2$—$CH_2$, 28H), 1.61 (t, $CH_2$—$CH_2$—C=O, 4H), 1.97 (t, —O—$CH_2$—$CH_2$—$CH_2$—O, 2H), 2.28 (t, $CH_2$—C=O, 4H), 4.15 (t, C(=O)—O—$CH_2$,4H).
Figure 2:
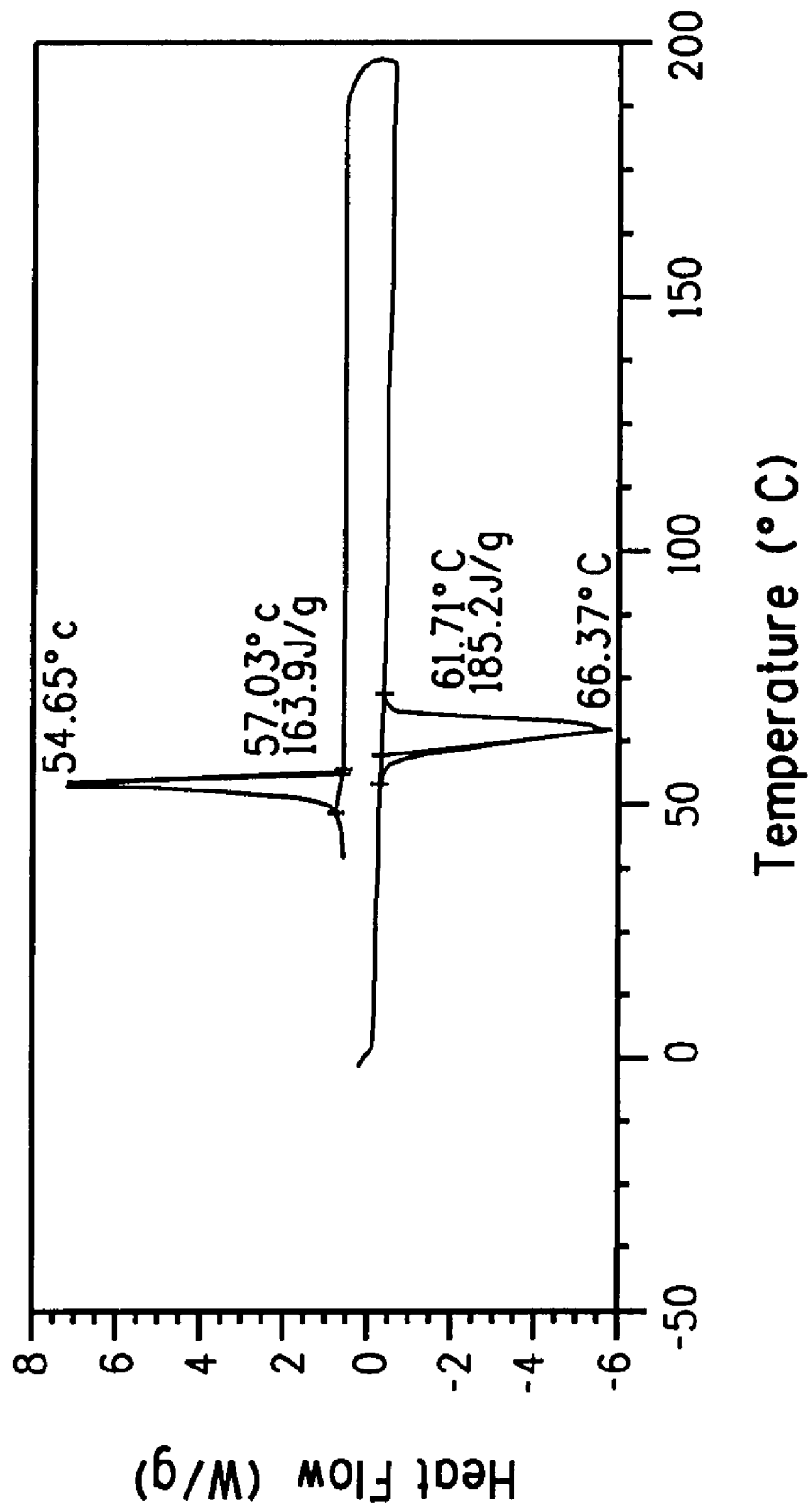
FIG. 2 is a DSC (Differential Scanning Calorimetry) curve of the product obtained in Example 3. DSC (Tm=66.4° C. and Tc=54.7° C.).
Figure 3:
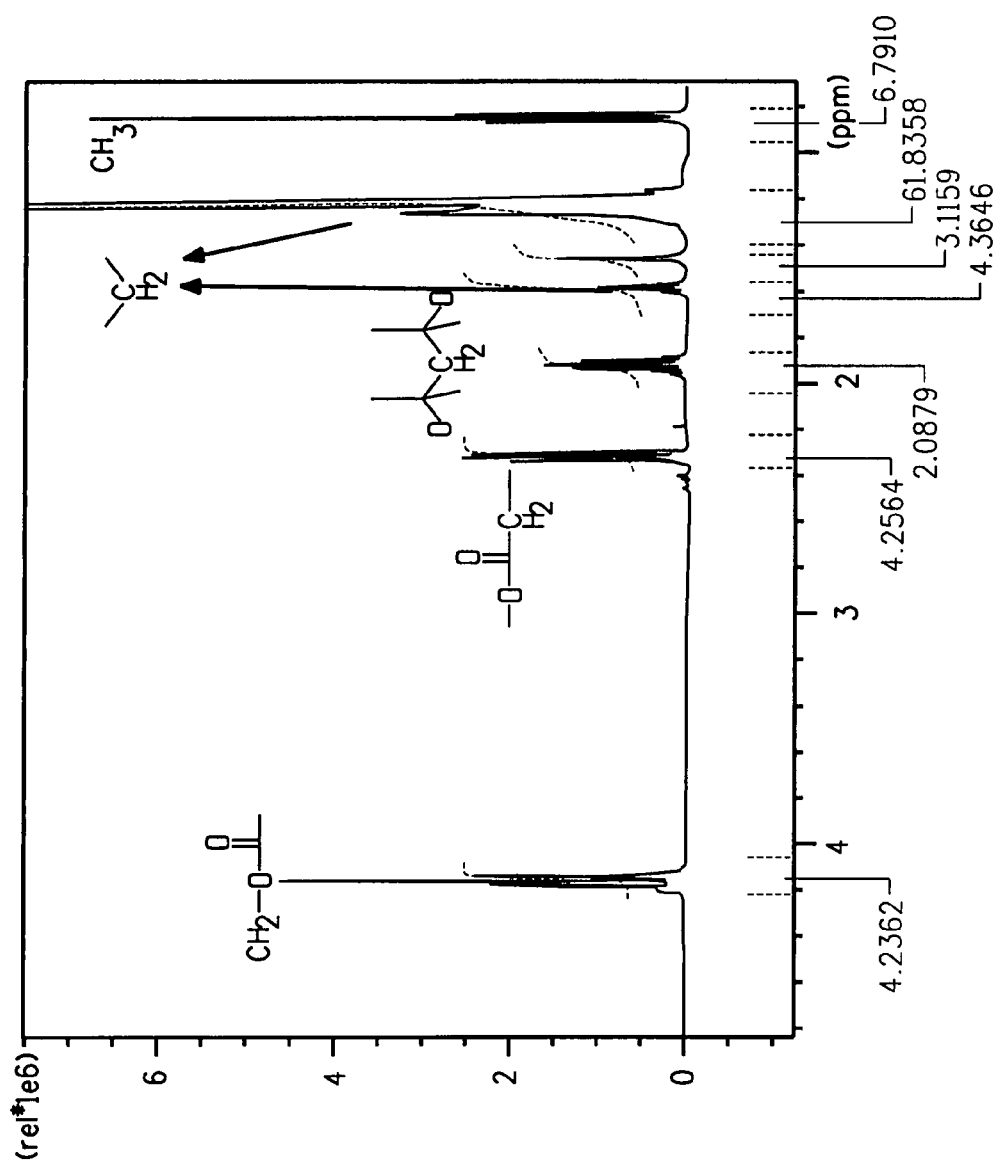
FIG. 3 is diagram of nuclear magnetic resonance spectra of the products obtained in example 4. The figure plots the following values: δ=0.88 (t, CH$_3$—CH$_2$, 6H), 1.26 (t, CH$_2$—CH$_2$—CH$_2$, 28H), 1.61 (t, CH$_2$—CH$_2$—C═O, 4H), 1.97 (t, —O—CH$_2$—CH$_2$—CH$_2$—O, 2H), 2.28 (t, CH$_2$—C═O, 4H), 4.15 (t, C(═O)—O—CH$_2$-4H).

The transformed *E. coli* DH5α containing cosmid pKP1 containing a portion of the *Klebsiella* genome encoding the glycerol dehydratase enzyme was deposited on 18 Apr. 1995 with the ATCC under the terms of the Budapest Treaty and is identified by the ATCC number ATCC 69789. The transformed *E. coli* DH5α containing cosmid pKP4 containing a portion of the *Klebsiella* genome encoding a diol dehydratase enzyme was deposited on 18 Apr. 1995 with the ATCC under the terms of the Budapest Treaty and is identified by the ATCC number ATCC 69790. As used herein, "ATCC" refers to the American Type Culture Collection international depository located at 10801 University Boulevard, Manassas, Va., 20110 2209, U.S.A. The "ATCC No." is the accession number to cultures on deposit with the ATCC.

DETAILED DESCRIPTION OF THE INVENTION

All references cited within this disclosure are incorporated herein by reference in their entirety. The fatty acid monoester and diester of 1,3-propanediol produced in a way that does not substantially increase the net amount of carbon dioxide are useful in the preparation of medicines, soaps, detergents, shampoos and personal care or cosmetic products. In such products, fatty acid monoesters and diesters of 1,3-propanediol can specifically be used as emulsifier, surfactant, conditioner, structurant, thickener, humectant, temperature stabilizer, chemical stabilizers, opacificer, or pearlizing agent.

Fatty acid monoesters and diesters of biologically-produced 1,3 propanediol are formed by esterification of biologically derived 1,3-propanediol. Biologically-derived 1,3-propanediol can be obtained through catalytic conversion of non-fossil fuel carbon via fermentation with an organism that is able to synthesize 1,3-propanediol. The process provides 1,3-propanediol and its conjugate monoesters and diesters without introducing additional carbon into the atmosphere during the production, use, or disposal of the material.

An aspect of the present invention provides a process to obtain fatty acid monoesters and diesters of biologically-produced 1,3 propanediol. Purified biologically-produced 1,3-propanediol can be obtained through catalytic conversion of non-fossil fuel carbon via fermentation with an organism that is able to synthesize 1,3-propanediol.

Biologically produced 1,3 propanediol represents a new feedstock for useful monoesters and diesters of 1,3 propanediol. Such monoesters and diesters have not previously been produced from a biosourced monomer. As such, this invention is directed to a new composition of matter, comprising 1,3 propanediol derived from biosourced carbon substrates. These compositions may be distinguished from similar compositions derived from all petrochemical carbon on the basis of biobased carbon content.

The terms used in this application shall be accorded the following definitions:

The terms, "bio-based PDO ester", "biologically-derived-PDO esters" and "biologically-based 1,3-propanediol esters" and similar terms as used herein refer to monoesters and diesters produced from biologically produced 1,3-propanediol.

The terms "bio-PDO", "bio-produced PDO", "biologically-produced 1,3-propanediol", "bio-derived 1,3-propanediol" and "biologically-derived 1,3-propanediol" and similar terms as used here in refer to 1,3-propanediol derived from microorganism metabolism of plant-derived sugars composed of carbon of atmospheric origin, and not composed of fossil-fuel carbon.

The terms 1,3-propanediol, 1,3-propane diol, 3G, propanediol, polyol, and PDO are all used interchangeably within this disclosure.

"Substantially purified," as used by applicants to describe the biologically-produced 1,3-propanediol produced by the process of the invention, denotes a composition comprising 1,3-propanediol having at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm.

"Biologically produced" means organic compounds produced by one or more species or strains of living organisms, including particularly strains of bacteria, yeast, fungus and other microbes. "Bio-produced" and biologically produced are used synonymously herein. Such organic compounds are composed of carbon from atmospheric carbon dioxide converted to sugars and starches by green plants.

"Biologically-based" means that the organic compound is synthesized from biologically produced organic components. It is further contemplated that the synthesis process disclosed herein is capable of effectively synthesizing other monoesters and diesters from bio-produced alcohols other than 1,3-propanediol; particularly including ethylene glycol, diethylene glycol, triethylene glycol, -, dipropylene diol, tripropylene diol, 2-methyl 1,3-propanediol, neopentyl glycol and bisphenol A. "Bio-based", and "bio-sourced"; "biologically derived"; and "bio-derived" are used synonymously herein.

"Fermentation" as used refers to the process of metabolizing simple sugars into other organic compounds. As used herein fermentation specifically refers to the metabolism of plant derived sugars, such sugar are composed of carbon of atmospheric origin.

"Carbon of atmospheric origin" as used herein refers to carbon dioxide molecules that have recently, in the last few decades, been free in the earth's atmosphere. Such carbons in mass are identifiable by the present of particular radioisotopes as described herein. "Green carbon", "atmospheric carbon", "environmentally friendly carbon", "life-cycle carbon", "biobased carbon", and carbon of atmospheric origin are used synonymously herein.

"Carbon of fossil origin" as used herein refers to carbon of petrochemical origin. Such carbon has not been exposed to UV rays as atmospheric carbon has, therefore masses of carbon of fossil origin has few radioisotopes in their population. Carbon of fossil origin is identifiable by means described herein. "Fossil fuel carbon", "fossil carbon", "polluting carbon", "petrochemical carbon", "petro-carbon", "petroleum-based carbon", and carbon of fossil origin are used synonymously herein.

"Naturally occurring" as used herein refers to substances that are derived from a renewable source and/or are produced by a biologically-based process.

"Fatty acid" as used herein refers to carboxylic acids that are often have long aliphatic tails, however, carboxylic acids of carbon length 1-40 are specifically included in this definition for the purpose of describing the present invention. "Fatty acid esters" as used herein are esters, which are composed of such, defined fatty acids.

"Catalyst" as used herein refers to a substance that is facilitates a chemical reaction without being either a reactant or a product of said reaction.

By the acronym "NMR" is meant nuclear magnetic resonance.

By the terms "color" and "color bodies" is meant the existence of visible color that can be quantified using a spectrocolorimeter in the range of visible light, using wavelengths of approximately 400-800 nm, and by comparison with pure water. Reaction conditions can have an important effect on the nature of color production. Examples of relevant conditions include the temperatures used, the catalyst and amount of catalyst. While not wishing to be bound by theory, we believe color precursors include trace amounts of impurities comprising olefinic bonds, acetals and other carbonyl compounds, peroxides, etc. At least some of these impurities may be detected by such methods as UV spectroscopy, or peroxide titration.

"Color index" refers to an analytic measure of the electromagnetic radiation-absorbing properties of a substance or compound.

"Hydrogenation reactor" refers to any of the known chemical reactors known in the literature, including but not limited to shaker-tubes, batch autoclaves, slurry reactors, up-flow packed bed, and trickle flow packed bed reactors.

A "b*" value is the spectrophotometrically determined "Yellow Blue measurement as defined by the CIE L*a*b* measurement ASTM D6290.

The abbreviation "AMS" refers to accelerator mass spectrometry.

The abbreviation "IRMS" refers to measurements of CO2 by high precision stable isotope ratio mass spectrometry.

The term "carbon substrate" means any carbon source capable of being metabolized by a microorganism wherein the substrate contains at least one carbon atom.

Unless otherwise stated, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed.

A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized in carbon dioxide. This radioactive isotope represents a small but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide which is released back to the atmosphere. Virtually all forms of life on Earth depend on this green plant production of organic molecule to produce the chemical energy that facilitates growth and reproduction. Therefore, the 14C that exists in the atmosphere becomes part of all life forms, and their biological products. These renewably based organic molecules that biodegrade to CO2 do not contribute to global warming as there is no net increase of carbon emitted to the atmosphere. In contrast, fossil fuel based carbon does not have the signature radiocarbon ratio of atmospheric carbon dioxide.

Assessment of the renewably based carbon in a material can be performed through standard test methods. Using radiocarbon and isotope ratio mass spectrometry analysis, the biobased content of materials can be determined. ASTM International, formally known as the American Society for Testing and Materials, has established a standard method for assessing the biobased content of materials. The ASTM method is designated ASTM-D6866.

When one molecule of renewably-based, biodegradable 1,3-propanediol biodegrades, three molecules of $CO_2$ are released into the atmosphere. Because all of these molecules of $CO_2$ released during biodegradation from fermentatively-derived 1,3-propanediol have an atmospheric origin, the net release of $CO_2$ to the atmosphere is thus zero. Comparatively, because a fossil fuel-derived 1,3-propanediol contains three carbon atoms, which originate from a fixed carbon source (i.e. the fossil fuel), degradation of one molecule of fossil fuel-derived 1,3-propanediol results in a net release of three molecules of $CO_2$ to the atmosphere.

The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of Biomass material present in the sample.

The terms "Renewably-based" or "biologically-derived" denote that the carbon content of the 1,3-propanediol is from a "new carbon" source as measured by ASTM test method D 6866-05 Determining the Biobased Content of Natural Range Materials Using Radiocarbon and Isotope Ratio Mass Spectrometry Analysis, incorporated herein by reference. This test method measures the C-14/C-12 isotope ratio in a sample and compares it to the C-14/C-12 isotope ratio in a standard 100% biobased material to give percent biobased content of the sample. "Biobased materials" are organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. A biobased material has a C-14/C-12 isotope ratio in range of from 1:0 to greater than 0:1. Contrarily, a fossil-based material, has a C-14/C-12 isotope ratio of 0:1.

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biomass content result is derived by assigning 100% equal to 107.5 pMC and 0% equal to 0 pMC. In this regard, a sample measuring 99 pMC will give an equivalent biobased content result of 93%.

Assessment of the materials described herein were done in accordance with ASTM-D6866. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of biobased component "present" in the material, not the amount of biobased material "used" in the manufacturing process.

Compositions produced in accordance with the invention comprise esters of 1,3-propanediol and an extraction product. The esters can a varying amount of biobased carbon depending on the compound used in the esterification. Biologically derived 1,3-propanediol contains biobased carbon. All three carbon atoms in 1,3 propanediol are biobased carbons. If the conjugate esters are formed using carboxylic acids that contain all biobased carbon, then the resulting esters also contain all biobased carbon. If, however, the carboxylic acids contain non-biobased carbons, i.e. carbons from a fossil fuel source, then the resulting ester will contain a percentage of biobased carbon in proportion to the number of carbons contributed from the carboxylic acid compared to the three carbons contributed from the biologically-derived 1,3-propanediol.

For example, distearate propanediol contains 39 carbon atoms, 18 from each of the stearic acid carbon chains and three from the 1,3-propanediol. Accordingly, if the strearic acid is non-biobased, 36 carbons out of the total 39 in distearate propanediol are non-biobased carbon. The predicted biobased content of distearate propanediol made from biologically-derived propanediol, and non-biologically derived strearic acid is 7.7 percent.

In an analysis performed using the ASTM-D6866 method, propylene glycol dibenzoate (BENZOFLEX® 284, Velsicol Chem. Corp. Rosemont, Ill.) was found to have 0% bio-based carbon content. The same analysis of propanediol dibenzoate, synthesized using biologically-derived 1,3-propanediol had 19% bio-based carbon content. The predicted bio-based carbon content propanediol dibenzoate made from biologically-derived 1,3 propanediol is 17.6%, which is within the standard deviation of the method.

If the stearic acid in the above example is biobased, the resulting distearate propanediol would have a biobased content of 100%. Accordingly, the conjugate esters of biologically-derived 1,3-propanediol have biobased content values proportional to the biobased content of the acids used to form the esters. The esters therefore can have biobased content of at least 3% biobased carbon, at least 6% biobased carbon, at least 10% biobased carbon, at least 25% biobased carbon, at least 50% biobased carbon, at least 75% biobased carbon, and 100% biobased carbon.

Biologically-derived 1,3-propanediol

Biologically-derived 1,3-propanediol is collected in a high purity form. Such 1,3-propanediol has at least one of the following characteristics: 1) an ultraviolet absorption at 220 nm of less than about 0.200 and at 250 nm of less than about 0.075 and at 275 nm of less than about 0.075; or 2) a composition having $L*a*b*$ "$b*$" color value of less than about 0.15 and an absorbance at 270 nm of less than about 0.075; or 3) a peroxide composition of less than about 10 ppm; or 4) a concentration of total organic impurities of less than about 400 ppm. A "$b*$" value is the spectrophotometrically determined Yellow Blue measurement as defined by the CIE $L*a*b*$ measurement ASTM D6290.

The level of 1,3-propanediol purity can be characterized in a number of different ways. For example, measuring the remaining levels of contaminating organic impurities is one useful measure. Biologically-derived 1,3-propanediol can have a purity level of less than about 400 ppm total organic contaminants; preferably less than about 300 ppm; and most preferably less than about 150 ppm. The term ppm total organic purity refers to parts per million levels of carbon-containing compounds (other than 1,3-propanediol) as measured by gas chromatography.

Biologically-derived 1,3-propanediol can also be characterized using a number of other parameters, such as ultraviolet light absorbance at varying wavelengths. The wavelengths 220 nm, 240 nm and 270 nm have been found to be useful in determining purity levels of the composition. Biologically-derived 1,3-propanediol can have a purity level wherein the UV absorption at 220 nm is less than about 0.200 and at 240 nm is less than about 0.075 and at 270 nm is less than about 0.075.

Biologically-derived 1,3-propanediol can have a b* color value (CIE $L*a*b*$) of less than about 0.15.

The purity of biologically-derived 1,3-propanediol compositions can also be assessed in a meaningful way by measuring levels of peroxide. Biologically-derived 1,3-propanediol can have a concentration of peroxide of less than about 10 ppm.

It is believed that the aforementioned purity level parameters for biologically-derived and purified 1,3-propanediol (using methods similar or comparable to those disclosed in U.S. Patent Application No. 2005/0069997) distinguishes such compositions from 1,3-propanediol compositions prepared from chemically purified 1,3-propanediol derived from petroleum sources.

1,3-propanediol produced biologically via fermentation is known, including in U.S. Pat. Nos. 5,686,276, 6,358,716, and 6,136,576, which disclose a process using a recombinantly-engineered bacteria that is able to synthesize 1,3-propanediol during fermentation using inexpensive green carbon sources such as glucose or other sugars from plants. These patents are specifically incorporated herein by reference. Biologically-derived 1,3-propanediol can be obtained based upon use of the fermentation broth generated by a genetically-engineered *Eschericia coli* (*E. coli*), as disclosed in U.S. Pat. No. 5,686,276. Other single organisms, or combinations of organisms, may also be used to biologically produce 1,3-propanediol, using organisms that have been genetically-engineered according to methods known in the art. "Fermentation" refers to a system that catalyzes a reaction between substrate(s) and other nutrients to product(s) through use of a biocatalyst. The biocatalysts can be a whole organism, an isolated enzyme, or any combination or component thereof that is enzymatically active. Fermentation systems useful for producing and purifying biologically-derived 1,3-propanediol are disclosed in, for example, Published U.S. Patent Application No. 2005/0069997 incorporated herein by reference.

The biologically derived 1,3-propanediol (bio-pdo) for use in the current invention, produced by the process described herein, contains carbon from the atmosphere incorporated by plants, which compose the feedstock for the production of bio-pdo. In this way, the bio-pdo contains only renewable carbon, and not fossil fuel based, or petroleum based carbon. Therefore the use of bio-pdo and its conjugate esters has less impact on the environment as the propanediol does not deplete diminishing fossil fuels. The use of the use of bio-pdo and its conjugate esters also does not make a net addition of carbon dioxide to the atmosphere, and thus does not contribute to greenhouse gas emissions. Accordingly, the present invention can be characterized as more natural and having less environmental impact than similar compositions comprising petroleum based glycols.

Moreover, as the purity of the bio-pdo utilized in the compositions of the invention is higher than chemically synthesized pdo and other glycols, risk of introducing impurities that may cause irritation is reduced by its use over commonly used glycols, such as propylene glycol.

In one embodiment of the invention, a composition comprising 1,3-propanediol and an extraction product is provided, where the 1,3-propanediol is biologically derived. The biologically-derived 1,3-propanediol can have at least 85% biobased carbon, at least 95% biobased carbon, or 100% biobased carbon, when assessed by the application of ASTM-D6866 as described above.

A sample of biologically-derived 1,3-propanediol was analyzed using ASTM method D 6866-05. The results received from Iowa State University demonstrated that the above sample was 100% bio-based content. In a separate analysis, also performed using a ASTM-D6866 method, chemical, or petroleum-based 1,3-propanediol (purchased from SHELL) was found to have 0% bio-based content. Propylene glycol (USP grade from ALDRICH) was found to have 0% bio-based content.

It is contemplated herein that other renewably-based or biologically-derived glycols, such as ethylene glycol or 1,2 propylene glycol, diethylene glycol, triethylene glycol among others, can be used in the synthesis of the esters described.

There may be certain instances wherein a synthesis process may include use of a combination of a biologically-derived 1,3-propanediol and one or more non biologically-derived glycol components, such as, for example, chemically synthesized 1,3-propanediol. In such occasions, it may be difficult, if not impossible to determine which percentage of the glycol composition is biologically-derived, other than by calculating the bio-based carbon content of the glycol component. In this regard, the 1,3-propanediol used to form 1,3 propanediol esters, can comprise at least about 1% bio-based carbon content up to 100% bio-based carbon content, and any percentage there between.

Ester Conjugates of Biologically Derived 1,3-Propanediol

Esters of biologically derived 1,3-propanediol, "bio-PDO" can be synthesized by contacting bio-PDO with an organic acid. The organic acid can be from any origin, preferably either a biosource or synthesized from a fossil source. Most preferably the organic acid is derived from natural sources or bio-derived having formula $R_1R_2$—COOH. Where in the substituent $R_1$ can be saturated or unsaturated, substituted or unsubstituted, aliphatic or aromatic, linear or branched hydrocarbon having chain length 1 to 40 or their salts or alkyl esters. Where in the substituent $R_2$ can be H or COOH. The hydrocarbon chain can also have one or more functional groups such as alkene, amide, amine, carbonyl, carboxylic acid, halide, hydroxyl groups. Naturally occurring organic acids produced esters containing all biobased carbon. These naturally occurring organic acids, especially those produced by a biological organism, are classified as bio-produced and the resulting ester or diester could thereby also be classified as bio-produced. Naturally occurring sources of such fatty acids include coconut oil, various animal tallows, lanolin, fish oil, beeswax, palm oil, peanut oil, olive oil, cottonseed oil, soybean oil, corn oil, rape seed oil. Conventional fractionation and/or hydrolysis techniques can be used if necessary to obtain the fatty acids from such materials.

Appropriate carboxylic acids for producing esters of biologically-derived 1,3-propanediol generally include: (1) C1-C3 carbon containing mono carboxylic acids, including formic acid and acetic acid; (2) fatty acids, such as those acids containing four or more carbon atoms; (3) saturated fatty acids, such as butyric acid, caproic acid, valeric acid, caprylic acid, capric acid, lauric acid, myristic acid, palmitic acid, stearic acid, arachidic acid, and behenic acid; (4) unsaturated fatty acids, such as oleic acid, linoleic acid, and euricic acid; (5) polyunsaturated fatty acids, such as alpha-linolenic acid, stearidonic acid (or moroctic acid), eicosatetraenoic acid, omega-6 fatty acids, arachidonic acids, and omege-3 fatty acids, eicosapentaenoic acid (or timnodonic acid), dosocapentaenoic acid (or clupanodonic acid), and docosahexaenoic acid (or cervonic acid); (6) hydroxy fatty acids, such as 2-hydroxy linoleic acid, and recinoleic acid; phenylalkanoic fatty acids, such as 11-phenyl undecanoic acid, 13-phenyl tridecanoid acid, and 15-phenyl tridecanoid acid; and (7) cyclohexyl fatty acids, such as 11-cyclohexyl undecanoic acid, and 13-cyclohexyl tridecanoic acid.

The following acids and their salts or alkyl esters are specifically useful, acetic, butyric, lauric, myristic, palmitic, stearic, arachidic, adipic, benzoic, caprylic, maleic, palmitic, sebacic, archidonic, erucic, palmitoleic, pentadecanoic, heptadecanoic, nondecanoic, octadectetraenoic, eicosatetraenoic, eicosapentaenoic, docasapentaenoic, tetracosapentaenoic, tetrahexaenoic, docosahexenoic, (alpha)-linolenic, docosahexaenoic, eicosapentaenoic, linoleic, arachidonic, oleic, erucic, formic, propionic, valeric, caproic, capric, malonic, succinic, glutaric, adipic, pimelic, suberic, azelaic, tartaric, citric, salicylic, acetyl-salicylic, pelargonic, behenic, cerotic, margaric, montanic, melissic, lacceroic, ceromelissic, geddic, ceroplastic undecylenic, ricinoleic, and elaeostearic acid as well as mixtures of such acids. A more preferred list of suitable organic acids are acetic, adipic, benzoic, maleic, sebacic, and mixtures of such acids. A more preferred list of suitable "fatty acids" meaning generally acids named containing 8-40 carbon in the carbon useful in the present invention include butyric, valeric, caproic, caprylic, pelargonic, capric, lauric, myristic, palmitic, stearic, arachidic, behenic, cerotic, oleic, linoleic, linolenic, margaric, montanic, melissic, lacceroic, ceromelissic, geddic, ceroplastic and the mixtures of such acids. Among those acids, these acids, and their salts and alkyl esters are most preferred stearic, lauric, palmetic, oleic, 2-ethyl hexanoic, and 12-hydroxystearic and mixtures of such acids.

The esters produced include all the appropriate conjugate mono and diesters of 1,3 propanediol using the described organic acids. Some esters in particular that are produced include propanediol distearate and monostearate, propandiol dilaurate and monolaurate, propanediol dioleate and monooleate, propanediol divalerate and monovalerate, propanediol dicaprylate and monocaprylate, propanediol dimyristate and monomyristate, propanediol dipalmitate and monopalmitate, propanediol dibehenate and monobehenate, propanediol adipate, propanediol maleate, propanediol dibenzoate, propanediol diacetate, and all mixtures thereof.

In particular, the esters produced include: propanediol distearate and monostearate, propanediol dioleate and monooleate, propanediol dicaprylate and monocaprylate, propanediol dimyristate and monomyristate, propanediol, and all mixtures thereof.

Generally 1,3-propanediol can be contacted, preferably in the presence of an inert gas reacted with a fatty acid or mixture of fatty acids or salts of fatty acids in the absence or presence of a catalyst or mixture of two or more catalysts, at temperatures ranging from 25° C. to 400° C.

During the contacting, water is formed and can be removed in the inert gas stream or under vacuum to drive the reaction complete. Any volatile byproducts can be removed similarly. When the reaction is complete, the heating can be stopped and cooled.

The catalyst can be removed preferably by dissolving and removing in deionized water. If catalyst can be removed by treating with deionized water, the reaction mixture is treated with aqueous solutions of acid or base to forms salts and removing the salts either by washing or filtering.

Further purification to obtain high purity fatty esters, preferably for pharmaceutical application can be carried out by dissolving in a solvent that dissolves fatty ester easily at higher temperatures and least at lower temperatures and recrystallyzing with or without addition of additional solvent at low temperatures.

The catalyst can be an acid for non-limiting examples, sulfuric acid, or p-toluene sulfonic acid. The catalyst can also be a base, for non-limiting example, sodium hydroxide. The catalyst can also be a salt, for non-limiting example, potassium acetate. The catalyst can also be an alkoxide, for non-limiting example, titanium tetraisopropoxide. The catalyst can also be a heterogeneous catalyst, for non-limiting examples: zeolite, heteropolyacid, amberlyst, or ion exchange resin. The catalyst can also be a metal salt, for non-limiting examples, tin chloride, or copper chloride. The catalyst can also be an enzyme, such as those known in the art. The catalyst can also be an organic acid, for a non-limiting example, formic acid. Finally the catalyst can also be an organometalic compound, for non-limiting example, n-butyl-stannoic acid.

This process can be carried out in the presence or absence of a solvent. If a solvent is not necessary to facilitate the production of fatty ester, it is preferred that the process is carried out in the absence of solvent.

The process can be carried out at atmospheric pressure or under vacuum or under pressurized conditions.

Reaction 1 (diester)

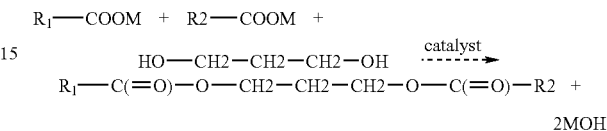

Where $R_1$ and $R_2$ is a hydrocarbon, preferably with a carbon chain length of about 1 to about 40. Such hydrocarbons can be saturated or unsaturated, substituted or unsubstituted, linear or branched M is hydrogen, an alkali metal or an alkyl group.

Reaction 2 (monoester)

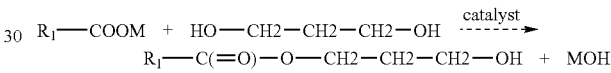

Where $R_1$ is a hydrocarbon, preferably with a carbon chain length of about 1 to about 40. Such hydrocarbons can be saturated or unsaturated, substituted or unsubstituted, linear or branched. M is hydrogen, an alkali metal or an alkyl group.

Compositions in accordance with the invention comprise esters in which R1 has one or more functional groups selected from the group consisting of alkene, amide, amine, carbonyl, carboxylic acid, halide, hydroxyl groups, ether, alkyl ether, sulfate and ethersulfate. The esters can have the formula R1—C(=O)—O—CH2—CH2—CH2—O—C(=O)—R2, wherein both R1 and R2 are linear or branched carbon chains of a length between about 1 an about 40 carbons. R1 and R2 can have one or more functional groups selected from the group consisting of alkene, amide, amine, carbonyl, carboxylic acid, halide, hydroxyl groups, ether, alkyl ether, sulfate and ethersulfate. Additionally, R1 and R2 can be the same carbon chain in the case of a diester.

Any molar ratio of diol to dicarboxylic acid or its salt or its ester can be used. The preferred range of the diol to dicarboxylic acid is from about 1:3 to about 2:1. This ratio can be adjusted to shift the favor of the reaction from monoester production to diester production. Generally, to favor the production of diesters slightly more than about a 1:2 ratio is used; whereas to favor the production of monoesters about a 1:1 ratio is used. In general, if the diester product is desired over the monoester the ratio of diol to dicarboxylic acid can range from about 1.01:2 to about 1.1:2; however if the monoester is desired a range of ratios from about 1.01:1 to about 2:1 is used.

The catalyst content for the reaction can be from 1 ppm to 60 wt % of the reaction mixture, preferably from 10 ppm to 10 wt %, more preferably from 50 ppm to 2 wt % of the reaction mixture.

The product may contain diesters, monoesters or combination diesters and monoesters and small percentage of unreacted acid and diol depending on the reaction conditions. Unreacted diol can be removed by washing with deionized water. Unreacted acid can be removed by washing with deionized water or aqueous solutions having base or during recrystallization.

Any ester of 1,3-propanediol can be made or used in accordance with the present invention. Short, middle and long chain monoesters and diesters of the 1,3-propanediol can be made. Specifically those acids containing between about 1 and about 36 carbons in the alkyl chain can be produced. More specifically, the following monoesters and diesters can be produced: propanediol distearate (monostearate and the mixture), propandiol dilaurate (monolaurate and the mixture), propanediol dioleate (monooleate and the mixture), propanediol divalerate (monovalerate and the mixture), propanediol dicaprylate (monocaprylate and the mixture), propanediol dimyristate (monomyristate and the mixture), propanediol dipalmitate (monopalmitate and the mixture), propanediol dibehenate (monobehenate and the mixture), propanediol adipate, propanediol maleate, propanediol dibenzoate, and propanediol diacetate.

In one aspect of the invention, the process for forming an ester from 1,3-propanediol includes providing 1,3-propanediol with at least 90% biobased carbon, contacting the 1,3-propanediol with an acid. Contacting the 1,3-propanediol with the acid forms the ester, and the ester is recovered.

A catalyst can be used to facilitate the esterification process. The catalysts appropriate for use in this process can be categorized as acids, bases, salts, alkoxides, heterogeneous, catalysts, metal salts, enzymes, organic acids, or organometalic compounds. Specifically, the catalyst can be one or more members of the group consisting of sulfuric acid, or p-toluene sulfonic acid, sodium hydroxide, potassium acetate, titanium tetraisopropoxide, zeolite, heteropolyacid, amberlyst, ion exchange resin, tin chloride, or copper chloride, formic acid, and n-butylstannoic acid.

The acid used in the esterification process can be an organic acid with the formula R—COOH, where R can be a saturated or unsaturated, substituted or unsubstituted, linear or branched or aromatic hydrocarbon having chain length 1 to 40, or its salts or its alkly and or aryl esters. Additionally, the substituent R can have one or more functional groups such as alkene, amide, amine, carbonyl, carboxylic acid, halide, hydroxyl groups, ether, alkyl ether, sulfate and ethersulfate.

The organic acid used can be a naturally occurring organic acid. The organic acid can be acetic, butyric, lauric, myristic, palmitic, stearic, arachidic, adipic, benzoic, caprylic, maleic, palmitic, sebacic, archidonic, erucic, palmitoleic, pentadecanoic, heptadecanoic, nondecanoic, octadectetraenoic, eicosatetraenoic, eicosapentaenoic, docasapentaenoic, tetracosapentaenoic, tetrahexaenoic, docosahexenoic, (alpha)-linolenic, docosahexaenoic, eicosapentaenoic, linoleic, arachidonic, oleic, erucic, formic, propionic, valeric, caproic, capric, malonic, succinic, glutaric, adipic, pimelic, suberic, azelaic, tartaric, citric, salicylic, acetyl-salicylic, pelargonic, behenic, cerotic, margaric, montanic, melissic, lacceroic, ceromelissic, geddic, ceroplastic, undecylenic, ricinoleic, elaeostearic acid, or mixtures thereof.

Specifically, the esterification process can be done using acetic, adipic, benzoic, maleic, sebacic, butyric, valeric, caproic, caprylic, pelargonic, capric, lauric, myristic, palmitic, stearic, arachidic, behenic, cerotic, oleic, linoleic, linolenic, margaric, montanic, melissic, lacceroic, ceromelissic, geddic, ceroplastic acids or mixtures thereof. Preferably, the organic acid is stearic, lauric, palmetic, oleic, 2-ethyl hexanoic, 12-hydroxystearic acid, or mixtures thereof.

In a particular embodiment, the organic acid is steric acid or oleic acid and the ester recovered is greater than 5% biobased carbon. In another specific embodiment, the organic acid is lauric acid and the ester recovered is greater than 10% biobased carbon.

The esterification process can be performed using 1,3-propanediol that has at least 95% biobased carbon, or has 100% biobased carbon.

In another aspect of the invention. The process for producing an ester, either or both a monoester and a diester, from biologically-produced 1,3-propanediol, comprises providing 1,3-propanediol produced biologically through fermentation and catalytic conversion of atmospheric carbon, contacting the 1,3-propanediol with an organic acid, and recovering the ester produced.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations used is as follows: "min" means minute(s), "sec" means second(s), "h" means hour(s), "μL" means microliter(s), "mL" means milliliter(s), "L" means liter(s), "nm" means nanometer(s), "mm" means millimeter(s), "cm" means centimeter(s), "□m" means micrometer(s), "mM" means millimolar, "M" means molar, "mmol" means millimole(s), "μmole" means micromole(s), "g" means gram(s), "μg" means microgram(s), "mg" means milligram(s), "g" means the gravitation constant, "rpm" means revolutions per minute, "SEM" means standard error of the mean, "vol %" means volume percent and "NMR" means nuclear magnetic resonance.

The meaning of abbreviations used is as follows "% wt." means percent by weight; "qs" means as much as suffices; "EDTA" means ethylenediamine tetraacetate; "° C." means degrees Centigrade; "° F." is degrees Fahrenheit, "Bio-PDO" means biologically-derived 1,3-propanediol; "ppm" is parts per million; "AU" is absorbance unit; "nm" is nanometer(s); "GC" is gas chromatograph; "APHA" is American Public Health Association; "cps" is centipoise; "f/t" is freeze/thaw; "mPa·s" is millipascal seconds; "D.I." is deionized.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. 3. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology* , Second Edition, Sinauer Associates, Inc., Sunderland, Mass., 1989.

All reagents, restriction enzymes and materials used for the growth and maintenance of bacterial cells were obtained from Aldrich Chemicals (Milwaukee, Wisc.), BD Diagnostic Systems (Sparks, Md.), Life Technologies (Rockville, Md.), or Sigma Chemical Company (St. Louis, Mo.), unless otherwise specified.

Glycerol used in the production of 1,3-propanediol was obtained from J. T. Baker Glycerin USP grade, Lot J25608 and G19657.

Differential Scanning Calorimetry: DSC thermograms were recorded using Universal V3 1A TA instrument under constant stream of nitrogen with a heating and cooling rate of 10° C./min.

NMR: 1H NMR spectra were recorded on Bruker DRX 500 using XWINNMR version 3.5 software. Data was acquired using a 90 degree pulse (p1) and a 30 second recycle delay (d11). Samples were dissolved in deuterated chloroform and nondeuterated chloroform was used as internal standard.

Isolation and Identification Bio-PDO

The conversion of glycerol to was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 N H2SO4 as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of bio-PDO was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated from glycerol were compared to that of authentic 1,3-propanediol (m/e: 57, 58).

Production of bio-based monoesters and diesters from bio-produced 1,3-propanediol Monoesters and diester of bio-produced 1,3-propandiol may be produced by combining bioPDO with organic acid. The combination is to be preformed in dry conditions under heat and prolong agitation with a selected catalyst. The ratio of monoester to diester produced will vary according to the molar ratio of acid to bioPDO and the selection of catalyst.

The production of esters was confirmed using $^1$H nuclear magnetic resonance. Analyses were performed using standard techniques and materials available to one of skill in the art of $^1$H NMR.

Proton Nuclear Magnetic Resonance ($^1$H NMR) Spectroscopy is a powerful method used in the determination of the structure of unknown organic compounds. It provides information concerning: the number of different types of hydrogens present in the molecule, the electronic environment of the different types of hydrogens and the number of hydrogen "neighbor" a hydrogen has.

The hydrogens bound to carbons attached to electron withdrawing groups tend to resonate at higher frequencies from TMS, tetramethylsilane, a common NMR standard. The position of where a particular hydrogen atom resonates relative to TMS is called its chemical shift ($\delta$). Typical chemicals shifts of fatty ester are as follows.

$\delta$=0.88 for terminal $CH_3$ $\delta$=1.26, 1.61 and 1.97 for methylene groups of ($-CH_2-CH_2-CH_2$), ($CH_2-CH_2-C=O$) and ($O-CH_2-CH_2-CH_2-O$) respectively, $\delta$=2.28 for methylene group adjustcent to ester ($CH_2-C=O$)

$\delta$=4.15 for ester ($C(=O)-O-CH_2-$).

Proton NMR can distinguish the protons corresponding to the end groups ($CH_2-OH$) ($\delta$=3.7) from that of the middle ester groups ($CH_2-O-C(=O)-$) ($\delta$=4.15 and 4.24 for diester and monoester, respectively) and thus it is possible to identify ester and can monitor the reaction by comparing the integral areas of these two peaks.

$$\% \text{ Esterification} = \frac{\text{Combined areas of peaks at 41.5 and 4.24} \times 100}{\text{Combined areas of peaks at 3.70, 41.5 and 4.24}}$$

Example 1

Conversion of D-glucose to 1,3-Propanediol Under Fermentation Conditions

*E. coli* strain ECL707, containing the *K. pneumoniae* dha regulon cosmids pKP1 or pKP2, the *K. pneumoniae* pdu operon pKP4, or the Supercos vector alone, is grown in a 5 L Applikon fermenter for the production of 1,3-propanediol from glucose.

The medium used contains 50-100 mM potassium phosphate buffer, pH 7.5, 40 mM (NH4)2SO4, 0.1% (w/v) yeast extract, 10 μM CoCl2, 6.5 μM CuCl2, 100 μM FeCl3, 18 μM FeSO4, 5 μM H3BO3, 50 μM MnCl2, 0.1 μM Na2MoO4, 25 μM ZnCl2, 0.82 mM MgSO4, 0.9 mM CaCl2, and 10-20 g/L glucose. Additional glucose is fed, with residual glucose maintained in excess. Temperature is controlled at 37° C. and pH controlled at 7.5 with 5N KOH or NaOH. Appropriate antibiotics are included for plasmid maintenance. For anaerobic fermentations, 0.1 vvm nitrogen is sparged through the reactor; when the dO setpoint was 5%, 1 vvm air is sparged through the reactor and the medium is supplemented with vitamin B12.

Titers of 1,3-propanediol (g/L) range from 8.1 to 10.9. Yields of bio-PDO (g/g) range from 4% to 17%.

Example 2

Purification of Biosourced 1.3-Propanediol

Published U.S. Patent Application No. 2005/0069997 discloses a process for purifying 1,3-propanediol from the fermentation broth of a cultured *E. coli* that has been bioengineered to synthesize 1,3-propanediol from sugar. The basic process entails filtration, ion exchange and distillation of the fermentation broth product stream, preferably including chemical reduction of the product during the distillation procedure.

1,3-Propanediol, produced as recited in Example 1, was purified, by a multistep process including broth clarification, rotary evaporation, anion exchange and multiple distillation of the supernatant.

At the end of the fermentation, the broth was clarified using a combination of centrifugation and membrane filtration for cell separation, followed by ultrafiltration through a 1000 MW membrane. The clarified broth processed in a large rotary evaporator. Approximately 46 pounds of feed material (21,000 grams) were processed to a concentrated syrup. A 60 ml portion of syrup was placed in the still pot of a 1" diameter distillation column. Distillation was conducted at a vacuum of 25 inches of mercury. A reflux ratio of approximately 1 was used throughout the distillation. Several distillate cuts were taken, the central of which received further processing. The material was diluted with an equal volume of water, the material was loaded onto an anion exchange column (mixed bed, 80 grams of NM-60 resin), which had been water-washed. Water was pumped at a rate of 2 ml/min, with fractions being collected every 9 minutes. Odd number fractions were analyzed, and fractions 3 through 9 contained 3G. The fractions containing 3G were collected and subjected to microdistillation to recover several grams of pure 1,3-propanediol monomer (which was polymerized to mono and diesters according the methods described in Example 2-8).

Example 3

Production of Propanediol Distearate Using P-toluenesulfonic acid as catalyst

To prepare propanediol distearate from biosource 1,3-propanediol and stearic acid, biosource 1,3-propanediol was purified using methods as in examples 1 and 2. 2.58 g (0.033 moles) of biosource 1,3-propanediol, 19.45 g (0.065 moles) of stearic acid (Aldrich, 95%), and 0.2125 g (0.001 moles) of p-toluenesulfonic acid (Aldrich 98.5%) were charged into glass reactor fitted with mechanical stirrer and the reactor was flushed with dry nitrogen gas to remove air and moisture for 15 min. Then reaction temperature was raised to 100° C. while thoroughly stirring the reaction mixture under nitrogen flow and continued for 210 min.

After completion of the reaction, reaction mixture was cooled to about 35° C. and the product was transferred into a beaker. The product was purified by adding 100 mL of water and thoroughly stirring at 45-60° C., to form an emulsion for 15 min. The mixture was cooled and the solid propanediol distearate was separated by filtration.

The product was characterized by $^1$H NMR (Nuclear Magnetic Resonance) spectra (CDCl$_3$ (deuterated chloroform)): δ=0.88 (t, CH$_3$—CH$_2$, 6H), 1.26 (t, CH$_2$—CH$_2$—CH$_2$, 28H), 1.61 (t, $\overline{CH_2}$—CH$_2$—C=O, 4H), 1.97 ($\overline{t}$, —O—CH$_2$—CH$_2$—CH$_2$—O, 2H), 2.28 (t, CH$_2$—C=O, 4H), 4.15 (t, C(=O)—O—CH$_2$-4H) and DSC (Tm=66.4° C. and Tc=54.7° C.).

Example 4

Purity Characterizations of Biologically-Derived 1.3-Propanediol

In Table 1 below, biologically-derived 1,3-propanediol (produced and purified as described in Published U.S. Patent Application No. 2005/0069997) ("Bio-PDO") is compared, in several purity aspects, to two separate commercially-obtained preparations of chemically-produced 1,3-propanediol (Source A and B).

TABLE 1

|  | Units | Source A | Source B | Bio-PDO |
|---|---|---|---|---|
| Total Org Impurities | ppm | 570 | 695 | 80 |
| UV Abs 220 nm, | AU | 0.25 | 1.15 | 0.12 |
| UV Abs 250 nm, | AU | 0.123 | 0.427 | 0.017 |
| UV Abs 275 nm | AU | 0.068 | 0.151 | 0.036 |
| UV Abs 350 nm | AU | 0.013 | 0.007 | 0.001 |
| Peroxides | ppm | 67 | 43 | 2 |
| CIE L*a*b* ASTM D6290 | b* | 0.411 | 0.03 | 0.1 |
| Carbonyls | ppm | 147 | 175 | 1 |

A typical profile of purity aspects are provided in Table 2 below, on a sample of biologically-produced 1,3-propanediol purified by a process disclosed in Published U.S. Patent Application No. 2005/0069997.

TABLE 2

|  | Units |  |
|---|---|---|
| 1,3-Propanediol | GC area % | 99.992 |
| pH, neat | pH | 8.22 |
| UV Abs. @ 270 nm, 1:5 dilution | AU | 0.01 |
| Color APHA |  | 3 |
| Color (Process Measurement) L*a*b* | b* | 0.10 |
| Water | ppm | 115 |
| UV abs 220 nm neat | AU | 0.144 |
| UV abs 250 nm neat | AU | 0.017 |
| UV abs 275 nm neat | AU | 0.036 |
| UV abs 350 nm neat | AU | 0.001 |
| Peroxide | ppm | 2 |
| Metals | ppm | <1 |
| Sulfur | ppm | <1 |
| Carbonyl | ppm | 1 |

The unit ppm of total organic impurities means parts per million of total organic compounds in the final preparation, other than 1,3-propanediol, as measured by a gas chromatograph with a flame ionization detector. Results are reported by peak area. A flame ionization detector is insensitive to water, so the total impurity is the sum of all non 1,3-propanediol organic peaks (area %) ratioed to the sum of all area % (1,3-propanediol included). The term "organic materials" refers to the contaminants containing carbon.

The tables show that the disclosed method of purification provides for highly pure biologically derived 1,3-propanediol, as compared to commercially-obtained preparations of chemically-produced 1,3-propanediol.

Example 5

Production of propanediol distearate using p-toluenesulfonic acid as catalyst 39.61 g (0.133 moles) of stearic acid (Aldrich, 95%), 5.05 g (0.066 moles) of bio-source 1,3-propanediol (Bio-PDO) and 0.46 g (0.0024 moles) of p-toluenesulfonic acid were charged into glass reactor fitted with mechanical stirrer and the reactor was flushed with dry nitrogen gas to remove air and moisture for 15 min. Then reaction temperature was raised to 100° C. while thoroughly stirring the reaction mixture under nitrogen flow. When the reaction temperature reached 100° C., nitrogen flow was shut off and low vacuum was applied to remove by byproduct. The reaction was continued for 2 h. The vacuum was stopped and product was cooled under nitrogen flow.

The product was purified as described in Example 3 and recrystallized as described in Example 4.

Figure 4:
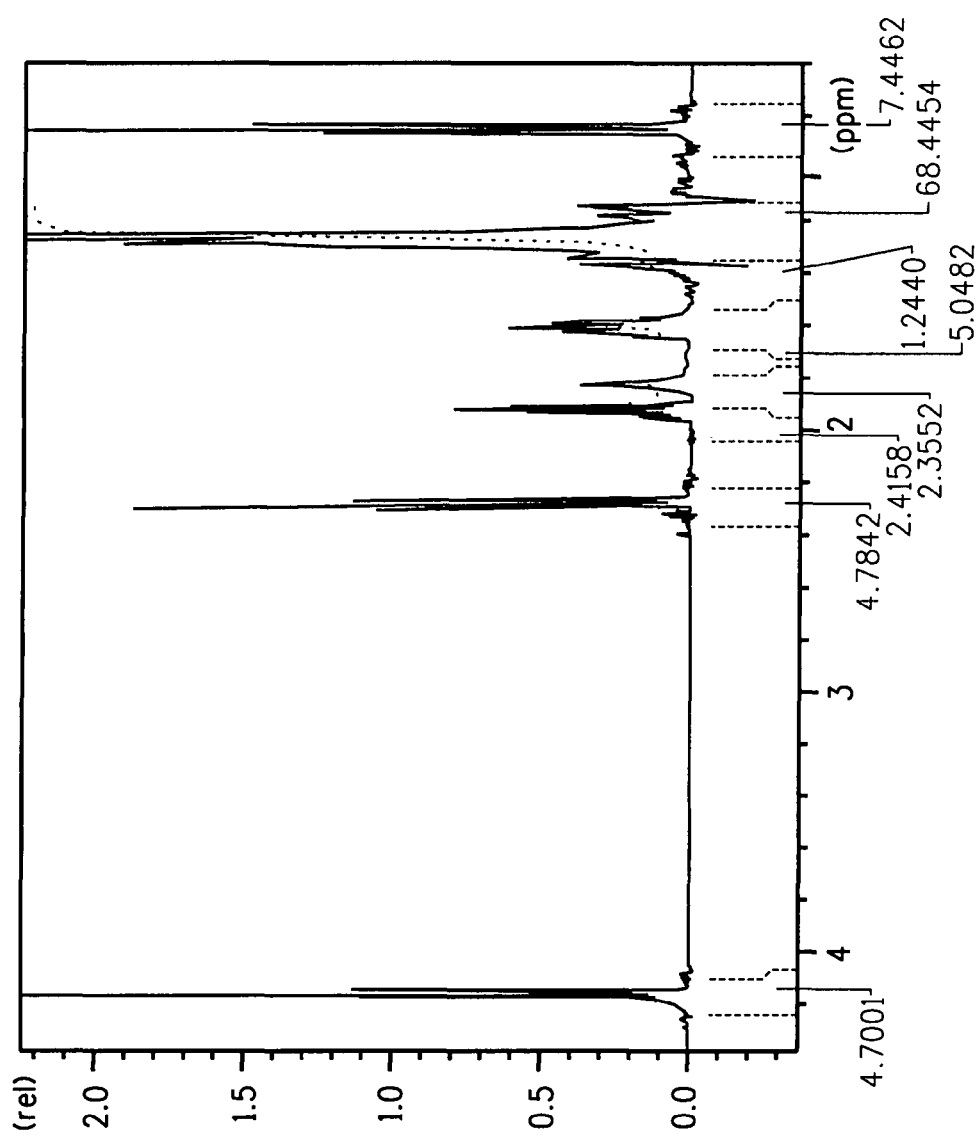
FIG. 4 is diagram of nuclear magnetic resonance spectra of the recrystallized products obtained in example 5. The figure plots the following values: δ=0.88 (t, CH$_3$—CH$_2$), 1.27 (t, CH$_2$—CH$_2$—CH$_2$), 1.60 (t, CH$_2$—CH$_2$—C═O), 1.87 and 1.96 (t, —O—CH$_2$—CH$_2$—CH$_2$—O,), 2.31 (t, CH$_2$—C═O,), 3.70 (t, HO—CH$_2$—CH$_2$—), 4.15 and 4.24 (t, C(═O)—O—CH$_2$—).

The product was characterized by 1H NMR spectra (CDCl$_3$): δ=0.88 (t, CH$_3$—CH$_2$, 6H), 1.26 (t, CH$_2$—CH$_2$—CH$_2$, 28H), 1.61 (t, CH$_2$—CH$_2$—C=O, 4H), 1.97 (t, —O—CH$_2$—CH$_2$—CH$_2$—O, 2H), 2.28 (t, CH$_2$—C=O, 4H), 4.15 (t, C(=O)—O—CH$_2$-4H). FIG. 4 depicts a graph of these data.

Example 6

Production of propanediol monostearate and propanediol distearate using tin chloride as catalyst 72.06 g (0.243 moles) of stearic acid (Aldrich, 95%), 9.60 g (0.126 moles) of 1,3-propanediol and 0.25 g of SnCl2 (Aldrich 98%) were charged into glass reactor fitted with mechanical stirrer and the reactor was flushed with dry nitrogen gas to remove air and moisture for 15 min. Then reaction temperature was raised to 120° C. while thoroughly stirring the reaction mixture under nitrogen flow and continued for 240 min.

After completion of the reaction, reaction mixture was cooled and analyzed by NMR. The product contained 39 mole % of propanediol monostearate, 19 mole % of propanediol distearate and 42 mole % 1,3-propanediol.

Figure 5:
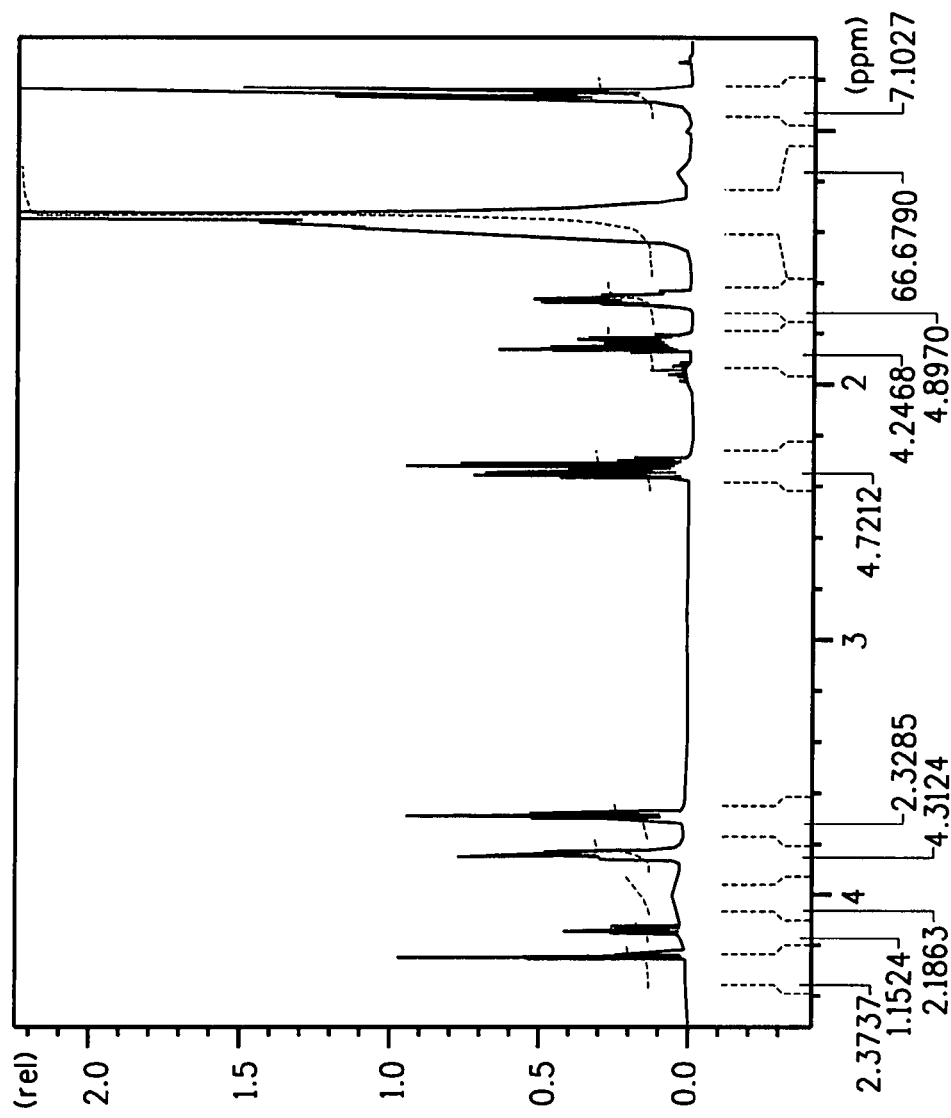
FIG. 5 is diagram of nuclear magnetic resonance spectra of the products obtained in example 6. The figure plots the following values: δ=0.88 (t, CH$_3$—CH$_2$), 1.27 (t, CH$_2$—CH$_2$—CH$_2$), 1.63 (t, CH$_2$—CH$_2$—C═O), 1.82, 1.87 and 1.96 (t, —O—CH$_2$—CH$_2$—CH$_2$—O,), 2.31 (t, CH$_2$—C═O,), 3.69 and 3.86 (t, HO—CH$_2$—CH$_2$—), 4.15 and 4.21 (t, C(═O)—O—CH$_2$—).

1H NMR spectra (CDCl$_3$) δ=0.88 (t, CH$_3$—CH$_2$), 1.27 (t, CH$_2$—CH$_2$—CH$_2$), 1.63 (t, CH$_2$—CH$_2$—C=O), 1.82, 1.87 and 1.96 (t, —O—CH$_2$—CH$_2$—CH$_2$—O,), 2.31 (t, CH$_2$—C=O,), 3.69 and 3.86 (t, HO—CH$_2$—CH$_2$—), 4.15 and 4.21 (t, C(=O)—O—CH$_2$—). FIG. 5 depicts a graph of these data.

Example 7

Production of propanediol monostearate and propanediol distearate using titanium tetraisopropoxide as catalyst 35.51 g (0.119 moles) of stearic acid (Aldrich, 95%), 9.55 g (0.125 moles) of 1,3-propanediol and 0.01 g of Ti(OC3H7)4 (Aldrich, 99.99%) were charged into glass reactor fitted with mechanical stirrer and the reactor was flushed with dry nitrogen gas to remove air and moisture for 15 min. Then reaction temperature was raised to 170° C. while thoroughly stirring the reaction mixture under nitrogen flow and continued for 240 min. Then the reaction was continued under vacuum for another 30 min. The vacuum was stopped and product was cooled under nitrogen flow and analyzed by NMR.

The product has 36 mole % propanediol monostearate and 64 mole % propanediol distearate.

Figure 6:
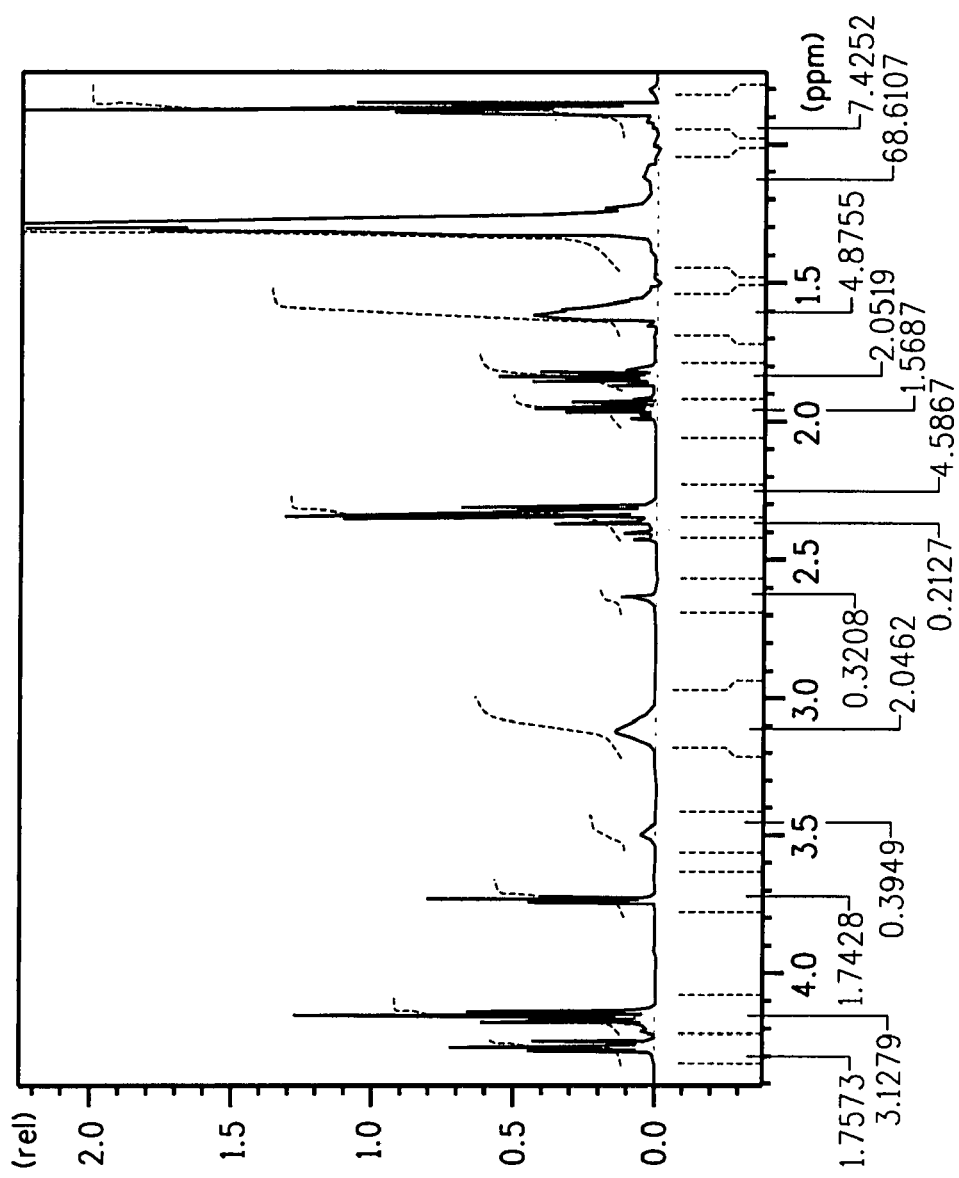
FIG. 6 is diagram of nuclear magnetic resonance spectra of the products obtained in example 7. The figure plots the following values: δ=0.88 (t, CH$_3$—CH$_2$), 1.27 (t, CH$_2$—CH$_2$—CH$_2$), 1.60 (t, CH$_2$—CH$_2$—C═O), 1.87 and 1.96 (t, —O—CH$_2$—CH$_2$—CH$_2$—O,), 2.31 (t, CH$_2$—C═O,), 3.70 (t, HO—CH$_2$—CH$_2$—), 4.15 and 4.24 (t, C(═O)—O—CH$_2$—).

1H NMR spectra (CDCl$_3$) δ=0.88 (t, CH$_3$—CH$_2$), 1.27 (t, CH$_2$—CH$_2$—CH$_2$), 1.60 (t, CH$_2$—CH$_2$—C=O), 1.87 and 1.96 (t, —O—CH$_2$—CH$_2$—CH$_2$—O,), 2.31 (t, CH$_2$—C=O,), 3.70 (t, HO—CH$_2$—CH$_2$—), 4.15 and 4.24 (t, C(=O)—O—CH$_2$—). FIG. 6 depicts a graph of these data.

Example 8

Production of propanediol monostearate and propanediol distearate using potassium acetate as catalyst 39.72 g (0.133 moles) of stearic acid (Aldrich, 95%), 10.12 g (0.133 moles) of bio-source 1,3-propanediol (Bio-PDO) and 2.47 g (0.025 moles) of potassium acetate (Aldrich, 99%) were charged into glass reactor fitted with mechanical stirrer and the reactor was flushed with dry nitrogen gas to remove air and moisture for 15 min.

Then reaction temperature was raised to 130° C. while thoroughly stirring the reaction mixture under nitrogen flow. The reaction was continued for 4 h under nitrogen flow. Then the nitrogen flow was shut off and vacuum was applied for 10 min before stopping the reaction. The obtained product was analyzed without further purification.

NMR analysis confirmed the product contained 64.7 mole % of propanediol monostearate, 9.7% mole % of Propanediol distearate and 25.6 mole % 1, 3 Propanediol.

Figure 7:
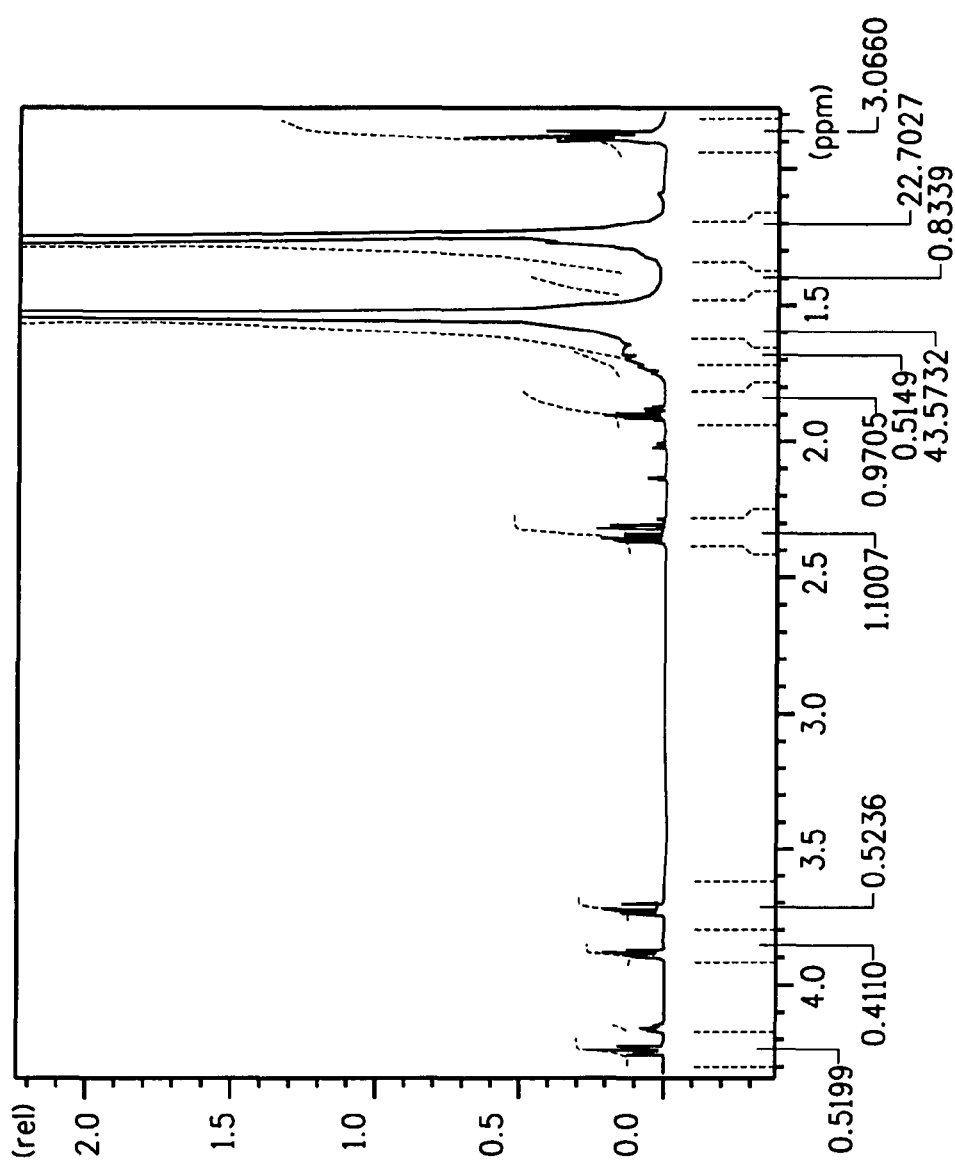
FIG. 7 is diagram of nuclear magnetic resonance spectra of the products obtained in example 8. The figure plots the following values: δ=0.88 (t, CH$_3$—CH$_2$), 1.27 (t, CH$_2$—CH$_2$—CH$_2$), 1.63 (t, CH$_2$—CH$_2$—C═O), 1.82, 1.87 and 1.96 (t, —O—CH$_2$—CH$_2$—CH$_2$—O,), 2.31 (t, CH$_2$—C═O,), 3.70 and 3.86 (t, HO—CH$_2$—CH$_2$—), 4.15 and 4.24 (t, C(═O)—O—CH$_2$—).

1H NMR spectra (CDCl$_3$) δ=0.88 (t, CH$_3$—CH$_2$), 1.27 (t, CH$_2$—CH$_2$—CH$_2$), 1.63 (t, CH$_2$—CH$_2$—C=O), 1.82, 1.87 and 1.96 (t, —O—CH$_2$—CH$_2$—CH$_2$—O,), 2.31 (t, CH$_2$—C=O,), 3.70 and 3.86 (t, HO—CH$_2$—CH$_2$—), 4.15 and 4.24 (t, C(=O)—O—CH$_2$—). FIG. 7 depicts a graph of these data.

Example 9

Production of propanediol dilaurate using p-toluenesulfonic acid as catalyst 50.2 g (0.246 moles) of lauric acid (Aldrich, 98%), 9.35 g (0.123 moles) of bio-source 1,3-propanediol (Bio-PDO) and 0.6 g (0.0031 moles) of p-toluenesulfonic acid (Aldrich 98.5%) were charged into glass reactor fitted with mechanical stirrer and the reactor was flushed with dry nitrogen gas to remove air and moisture for 15 min.

Then reaction temperature was raised to 130° C. while thoroughly stirring the reaction mixture under nitrogen flow. The reaction was continued for 4 h under nitrogen flow. After completion of the reaction, the product was cooled and 90 mL of 0.5 wt % sodium hydroxide solution was added and agitated at 40 to 50° C. for 10 min. Then the product was filtered and thoroughly washed with deionized water and dried.

NMR analysis confirmed the product contained 99.2 mole % of propanediol dilaurate 1H NMR spectra (CDCl$_3$) δ=0.88 (t, CH$_3$—CH$_2$), 1.27 (t, CH$_2$—CH$_2$—CH$_2$), 1.63 (t, CH$_2$—CH$_2$—C=O), 1.96 (t, —O—CH$_2$—CH$_2$—CH$_2$—O,), 2.28 (t, CH$_2$—C=O,), 4.15 (t, C(=O)—O—CH$_2$—)

Example 10

Production of propanediol dioleate using p-toluenesulfonic acid as catalyst 51.7 g (0.164 moles) of oleic acid (Aldrich, 90%), 6.26 g (0.082 moles) of bio-source 1,3-propanediol (Bio-PDO) and 0.6 g (0.0031 moles) of p-toluenesulfonic acid (Aldrich 98.5%) were charged into glass reactor fitted with mechanical stirrer and the reactor was flushed with dry nitrogen gas to remove air and moisture for 15 min.

Then reaction temperature was raised to 130° C. while thoroughly stirring the reaction mixture under nitrogen flow. The reaction was continued for 4 h under nitrogen flow. After completion of the reaction, the product was cooled and 90 mL of 0.5 wt % sodium hydroxide solution was added and agitated at 40 to 50° C. for 10 min.

The mixture was transferred into a separating funnel and 500 mL of deionized water added and mixture was allowed to form tow separate layers. Aqueous layer was removed.

Another 500 mL deionized water was added, the solution was mixed and aqueous layer was after two clear layer were formed. The process was repeated for one more time.

NMR analysis confirmed the product contained 99.2 mole % of propanediol dilaurate 1H NMR spectra (CDCl$_3$) δ=0.88 (t, CH$_3$—CH$_2$), 1.27 and 1.30 (CH$_2$—CH$_2$—CH$_2$), 1.63 (t, CH$_2$—CH$_2$—C=O), 1.96 (t, —O—CH$_2$—CH$_2$—CH$_2$—O,), 2.28 (t, CH$_2$—C=O, ), 4.15 (t, C(=O)—O—CH$_2$—), 5.35 (m CH$_2$—CH=CH—CH$_2$)

Although the invention is illustrated and described herein with reference to specific embodiments, the invention is not intended to be limited to the details shown. Rather, various modifications may be made in the details within the scope and range of equivalents of the claims and without departing from the invention.

Comparative Example 1

Production of propanediol distearate using chemical 1,3-propanediol and p-toluenesulfonic acid as catalyst Chemical 1,3-propanediol (Shell Chemical LP, Houston, Tex.) was prepared as described herein, specifically as described in Examples 1 and 2. 5.2 g (0.068 moles) of chemical 1,3-propanediol, 38.9 g (0.13 moles) of stearic acid (Aldrich, 95%), and 0.425 g (0.002 moles) of p-toluenesulfonic acid (Aldrich, 98.5%) were charged into glass reactor fitted with mechanical stirrer and the reactor was flushed with dry nitrogen gas to remove air and moisture for 15 min. Then reaction temperature was raised to 130° C. while thoroughly stirring the reaction mixture under nitrogen flow and continued for 195 min at 130° C.

The product was purified as described in Example 3. The product was further purified by dissolving in chloroform and recrystallizing by adding acetone at 15° C. The recrystallized product was filtered and dried.

The product was characterized by 1H NMR spectra (CDCl$_3$): δ=0.88 (t, CH$_3$—CH$_2$, 6H), 1.26 (t, CH$_2$—CH$_2$—CH$_2$, 28H), 1.61 (t, CH$_2$—CH$_2$—C=O, 4H), 1.97 (t, —O—CH$_2$—CH$_2$—CH$_2$—O, 2H), 2.28 (t, CH$_2$—C=O, 4H), 4.15 (t, C(=O)—O—CH$_2$-4H).

The NMR spectra of the product was compared to the spectra of product described in Example 5. No differences were found in the chemical structure of the esters synthesized biologically derived and chemically derived 1,3-propanediol.

What is claimed:

1. A process for forming an ester from 1,3-propanediol comprising:
   (a) providing 1,3-propanediol with at least 90% biobased carbon, wherein the biobased carbon has a C-14/C-12 isotope ratio in range of from 1:0 to greater than 0:1;
   (b) contacting the 1,3-propanediol with an acid, forming the ester; and
   (c) recovering the ester, wherein said ester has a lower anthropogenic CO$_2$ emission profile as compared to an ester formed from 1,3-propanediol with a biobased carbon content of 0%.

2. The process of claim 1 wherein the contacting of the 1,3-propanediol with an acid is in the presence of a catalyst.

3. The process of claim 2, wherein the catalyst can be categorized as a member of one or more of the categories selected from the group consisting of: acids, bases, salts, alkoxides, heterogeneous, catalysts, metal salts, enzymes, organic acids, and organometalic compounds.

4. The process of claim 2, wherein the catalyst is one or more members of the group consisting of sulfuric acid, or p-toluene sulfonic acid, sodium hydroxide, potassium acetate, titanium tetraisopropoxide, zeolite, heteropolyacid, amberlyst, ion exchange resin, tin chloride, or copper chloride, formic acid, and n-butylstannoic acid.

5. The process of claim 1 wherein the acid is an organic acid.

6. The process of claim 5 wherein, wherein the organic acid has the formula R—COOH, wherein the substituent R can be a saturated or unsaturated, substituted or unsubstituted, linear or branched or aromatic hydrocarbon having chain length 1 to 40.

7. The process of claim 5, wherein the organic acid has the formula R—COOH, and the substituent R can have one or more functional groups such as alkene, amide, amine, carbonyl, carboxylic acid, halide, hydroxyl groups, ether, alkyl ether, sulfate and ethersulfate.

8. The process of claim 5 wherein the organic acid is a naturally occurring organic acid.

9. The process of claim 5 wherein the organic acid is selected from the group consisting of: acetic, butyric, lauric, myristic, palmitic, stearic, arachidic, benzoic, caprylic, maleic, sebacic, palmitoleic, pentadecanoic, heptadecanoic, nondecanoic, octadectetraenoic, eicosatetraenoic, eicosapentaenoic, docasapentaenoic, tetra cosapentaenoic, tetrahexaenoic, (alpha)-linolenic, docosahexaenoic, linoleic, arachidonic, oleic, erucic, formic, propionic, valeric, caproic, capric, malonic, succinic, glutaric, adipic, pimelic, suberic, azelaic, tartaric, citric, salicylic, acetyl-salicylic, pelargonic, behenic, cerotic, margaric, montanic, melissic, lacceroic, ceromelissic, geddic, ceroplastic, undecylenic, ricinoleic, elaeostearic acid, and mixtures thereof.

10. The process of claim 5 wherein the organic acid is selected from the group consisting of acetic, adipic, benzoic, maleic, sebacic, butyric, valeric, caproic, caprylic, pelargonic, capric, lauric, myristic, palmitic, stearic, arachidic, behenic, cerotic, oleic, linoleic, linolenic, margaric, montanic, melissic, lacceroic, ceromelissic, geddic, ceroplastic, and mixtures thereof.

11. The process of claim 5 wherein the organic acid is selected from the group consisting of stearic, lauric, palmitic, oleic, 2-ethyl hexanoic, 12-hydroxystearic acid, and mixtures thereof.

12. The process of claim 5, wherein the organic acid is stearic acid.

13. The process of claim 1 wherein the 1,3-propanediol has at least 95% biobased carbon.

14. The process of claim 13 wherein the 1,3-propanediol has 100% biobased carbon.

15. The process of claim 1 wherein the ester has the formula R1-C(=O)—O—CH2-CH2-CH2-OH, wherein R1 is a linear branched, cyclic or aromatic.

16. The process of claim 1 wherein the ester has the formula R1-C(=O)—O—CH2-CH2-CH2-O—C(=O)-R2, wherein R1 and R2 are linear branched, cyclic or aromatic.

17. The process of claim 15 wherein R1 and R2 are the same carbon chain.

18. The process of claim 1, wherein the ester recovered is selected from one or more members of the group consisting of:
   i. propanediol distearate, monostearate and a mixture thereof;
   ii. propandiol dilaurate, monolaurate and a mixture thereof;
   iii. propanediol dioleate, monooleate and a mixture thereof;
   iv. propanediol divalerate, monovalerate and a mixture thereof;
   v. propanediol dicaprylate, monocaprylate and a mixture thereof;
   vi. propanediol dimyristate, monomyristate and a mixture thereof;

vii. propanediol dipalmitate, monopalmitate and a mixture thereof;

viii. propanediol dibehenate, monobehenate and a mixture thereof;

ix. propanediol adipate;

x. propanediol maleate;

xi. propanediol dibenzoate, and;

xii. propanediol diacetate.

19. A process for producing an ester, either or both a monoester and a diester, from biologically-produced 1,3-propanediol, comprising:

(a) providing 1,3-propanediol produced biologically through fermentation and catalytic conversion of atmospheric carbon, wherein the carbon has a C-14/C-12 isotope ratio in range of from 1:0 to greater than 0:1;

(b) contacting said 1,3-propanediol with an organic acid, wherein said ester is produced; and (c) recovering said ester, wherein said ester has a lower anthropogenic $CO_2$ emission profile as compared to an ester produced from 1,3-propanediol derived from petrochemical carbon.

20. The process of claim 19 wherein the biologically-produced 1,3-propanediol has at least one of the following characteristics: 1) an ultraviolet absorption of less than about 0.200 at 220 nm and less than about 0.075 at 250 nm and less than about 0.075 at 275 nm; 2) a composition having L*a*b* "b*" color value of less than about 0.15 and an absorbance of less than about 0.075 at 270 nm; 3) a peroxide composition of less than about 10 ppm; and 4) a concentration of total organic impurities of less than about 400 ppm.

21. The process of claim 19 wherein the organic acid is steric acid or oleic acid and the ester recovered is greater than 5% biobased carbon.

22. The process of claim 19 wherein the organic acid is lauric acid and the ester recovered is greater than 10% biobased carbon.

* * * * *

UNITED STATES PATENT AND TRADEMARK OFFICE
CERTIFICATE OF CORRECTION

| | | |
|---|---|---|
| PATENT NO. | : 7,960,575 B2 | Page 1 of 1 |
| APPLICATION NO. | : 11/705245 | |
| DATED | : June 14, 2011 | |
| INVENTOR(S) | : Gyorgyi Fenyvesi | |

It is certified that error appears in the above-identified patent and that said Letters Patent is hereby corrected as shown below:

Column 21, line 63, delete the word "or".

Column 21, line 66, delete the word "or".

Column 22, line 3, delete the word "wherein,".

Column 24, line 10, delete the word ""b*"".

Column 24, line 15, the word "is" should be deleted and replaced with the word "has".

Column 24, line 18, the word "is" should be deleted and replaced with the word "has".

Signed and Sealed this
Fifteenth Day of November, 2011

David J. Kappos
*Director of the United States Patent and Trademark Office*